United States Patent [19]

Evans et al.

[11] Patent Number: 5,057,320
[45] Date of Patent: Oct. 15, 1991

[54] MEANS AND METHOD FOR INCREASING SKIN RESPIRATION

[75] Inventors: Gary W. Evans, Puposky, Minn.; Henry J. Peppler, Whitefish Bay, Wis.

[73] Assignee: Nutrition 21, San Diego, Calif.

[21] Appl. No.: 227,203

[22] Filed: Aug. 1, 1988

[51] Int. Cl.⁵ ............................................. A61L 15/16
[52] U.S. Cl. ................................... 424/447; 424/445; 514/277
[58] Field of Search ............... 424/443, 444, 445, 446, 424/447; 514/354, 277, 557

[56] References Cited

U.S. PATENT DOCUMENTS

| | | | |
|---|---|---|---|
| 2,320,478 | 6/1943 | Sperti | 424/195.1 |
| 3,976,781 | 8/1976 | Kalopissis | 514/538 |
| 4,062,855 | 12/1977 | Allan et al. | 424/419 |
| 4,085,217 | 4/1978 | Kalopissis | 514/354 |
| 4,109,000 | 8/1978 | Tanabe et al. | 514/354 |
| 4,126,445 | 11/1978 | Allan et al. | 514/568 |
| 4,133,887 | 1/1979 | Sherlock | 514/354 |
| 4,315,927 | 2/1982 | Evans | 514/188 |
| 4,438,099 | 3/1984 | Azzariti | 424/93 |

OTHER PUBLICATIONS

Goodson, W. et al., "Augmentation of Some Aspects of Wound Healing by a Skin Respiratory Factor", J. Surgical Research 21:125-129 (1976).
Kaplan, J., "Acceleration of Wound Healing by a Live Yeast Cell Derivative", Arch. Surg. 119:1005-1008 (1984).
"Live Yeast Cell Derivative", U.S. Federal Register 43:151, Washington, D.C.: GPO (Aug. 4, 1978).
Mirsky, et al., "Chromium in Biological Systems, I. Some Observations on Gluclose Tolerance Factor in Yeast", J. Inorg. Biochem. 13:11 (1980).
Krieger, I. and G. Evans, "Acrodermatitis Enteropathica Without Hypozincemia: Therapeutic Effect of a Pancreatic Enzyme Preparation Due to a Zinc-Binding Ligand", Journal of Pediatrics 96(1) 32-35 (1980).
Evans et al., "Purification and Characterization of a Zinc-Binding Ligand in Rat Intestine", (No. 89) Jour. Nutrition 109:xxii (Jan. 1979).
Johnson, P. and G. Evans, "Purification and Characterization of a Zinc-Binding Ligand in Human Milk", Federation Proceedings 38: 703, Abst. No. 2501 (Mar. 1979).
Johnson, P. E. and Evans, G. W., "Detection of Labile Zinc-Binding Ligands in Biological Fluids", Federation Proceedings 38: No. 2500 (Mar. 1979).
Krieger, et al., "A Variant of Acrodermatitis Enteropathica (AE) Hypozincemia, Therapeutic Effect of Pancreatic Enzyme Due to a Zinc Binding Ligand", J. Nutrition 109: xxi, Abst. No. 19 (Jan. 1979).

Primary Examiner—Thurman K. Page
Assistant Examiner—Leon R. Horne
Attorney, Agent, or Firm—Knobbe, Martens, Olson & Bear

[57] ABSTRACT

A method of enhancing mammalian skin respiration, and in particular promoting healing of injured skin, comprises supplying to the skin a composition consisting essentially of picolinic acid, or comprising picolinic acid in which composition is substantially free of impurities from yeast. The composition preferably provides at least 50,000 Units, and further preferably 500,000 Units, of Skin Respiratory Factor per gram of the composition.

15 Claims, 3 Drawing Sheets

MEANS AND METHOD FOR INCREASING SKIN RESPIRATION

FIELD OF THE INVENTION

This invention relates to medicine, particularly dermatology and, more particularly, to a method for enhancing respiration of mammalian skin, which has applications including promoting skin healing.

TECHNOLOGY REVIEW

It is known that human skin respires, obtaining oxygen from the bloodstream, as a function of the cell life in the skin tissue. Furthermore, the rate of respiration declines with age. Young skin respires more rapidly and absorbs greater quantities of oxygen. U.S. Pat. No. 2,320,478 to Sperti discloses the application of an extract from bakers' yeast to human skin, in order to increase respiration of skin cells, and apparently improve the cosmetic appearance of skin. The extract also produced increased respiration of rat skin. Both bakers' yeast and brewers' yeast are technically classified as *Saccharomyces cerevisiae*. The Sperti patent, and all other references cited herein, are incorporated by reference.

Methods have also been previously disclosed for accelerating wound healing. In particular, Goodson et al., *Journal of Surgical Research*, Vol. 21, p. 125-129 (1976), discloses a material described as "Skin Respiratory Factor", sometimes referred to as "SRF", which is a water soluble extract of brewer's yeast. As described in Goodson et al., SRF is an ingredient in a proprietary hemorrhoidal product, sold under the trademark PREPARATION H. Goodson et al evaluated the effect of SRF on wound healing since it had been shown to influence oxygen consumption by fibroblasts, and since it was known that some aspects of wound healing could be influenced by an agent altering oxygen consumption. The material studied by Goodson et al. contained 8100 Units of SRF per gram ("Units of SRF/g"), wherein 1 Unit of SRF increases the uptake of oxygen by minced rat abdominal skin (1 milligram dry weight) by 1% in a on hour measurement by Warburg manometry. In view of their in vitro and in vivo experiments, Goodson et al. concluded that the yeast extract tested was capable of stimulating wound oxygen consumption, epithelization, and collagen synthesis. Goodson et al also noted that the yeast extract produced early hair growth at wound sites treated with the extract.

Kaplan, *Arch. Surg.*, Vol. 119, p. 1005 (September 1984) investigated the extract used by Goodson et al., supra. Kaplan refers to the extract as live yeast cell derivative or LYCD, and examined its effect on the rate of burn wound healing in humans. Kaplan concluded that of LYCD was able to accelerate wound healing beyond its normal rate. Kaplan stated that the resulting stimulated angiogenesis, as well as the increase in oxygen consumption and collagen synthesis noted by Goodson et al., supra, may provide an explanation for the enhanced wound healing. This effect is also discussed in *Federal Register*, Vol. 43, No. 151 (August 4, 1978).

Other techniques for healing burned skin include that disclosed in U.S. Pat. No. 4,438,099 to Azzariti, which requires the application of a spray of *Candida kruseii* to burned skin, forming a crust over the wound. This is said to allow for a more rapid healing and skin regeneration in the affected area. The patent states that the treatment was also effective with open sores, such as varicose ulcers and decubitus ulcers.

It would be desirable then to have a means which enhances respiration of mammalian skin, since wound healing can be influenced by such a means. Further, a means which promotes healing of the skin would be useful in the treatment of skin injuries, such as burns and incisions.

SUMMARY OF THE INVENTION

The present invention provides a method and means for enhancing respiration of mammalian skin (which will be referred to simply as skin) and, in particular in promoting healing of injured skin. The invention is based on the discovery that picolinic acid (pyridine-2-carboxylic acid) enhances cell respiration which, as described above, is associated with promoting healing of a skin injury and promoting hair growth.

In the method of the present invention, a composition consisting essentially of picolinic acid or, alternatively, which comprises picolinic acid substantially free of impurities from yeast, is applied to skin. The compositions preferably exhibit at least 50,000 Units of SRF activity per gram, as defined above, and further preferably at least 500,000 Units of SRF activity, per gram of the composition.

Skin injuries which may be treated by the method include, but are not limited to, burns. In the performance of the present method, picolinic acid is typically provided in a carrier which is suitable for cutaneous application. For example, picolinic acid may be provided in an ointment, cream, lotion or spray.

Also contemplated is a dressing which can be applied to a skin injury, which dressing comprises a bandage and one of the picolinic acid compositions described. Further contemplated are compositions for topical application to the skin, comprising a suitable excipient for skin application and sufficient picolinic acid to provide the composition with at least about 25,000 Units of SRF activity per gram, preferably at least about 50,000 Units per gram and more preferably at least about 500,000 Units.

In treating skin, it is anticipated that compositions as described above will be applied to the wound for at least about ten days and then, depending upon the seriousness of the wound, up to 30 days or possibly more. Of course, in practice one would typically simply apply compositions of the present invention until the wound was completely, or near completely, healed.

When weights of picolinic are referred to, this includes both the anion or the corresponding portion of a compound such as picolinic acid, whether or not dissociated. Further, the total amount of picolinic acid in solution includes both dissociated and undissociated forms so that "picolinic acid" allows for adding to a solution, a picolinate compound which would produce free picolinate ions in water.

DRAWINGS

Embodiments of the invention will now be described, with reference to the drawings which generally show the effect of picolinic acid in increasing cell growth, and more particularly, in which.

DETAILED DESCRIPTION OF THE EMBODIMENTS OF THE INVENTION

Figure 1:
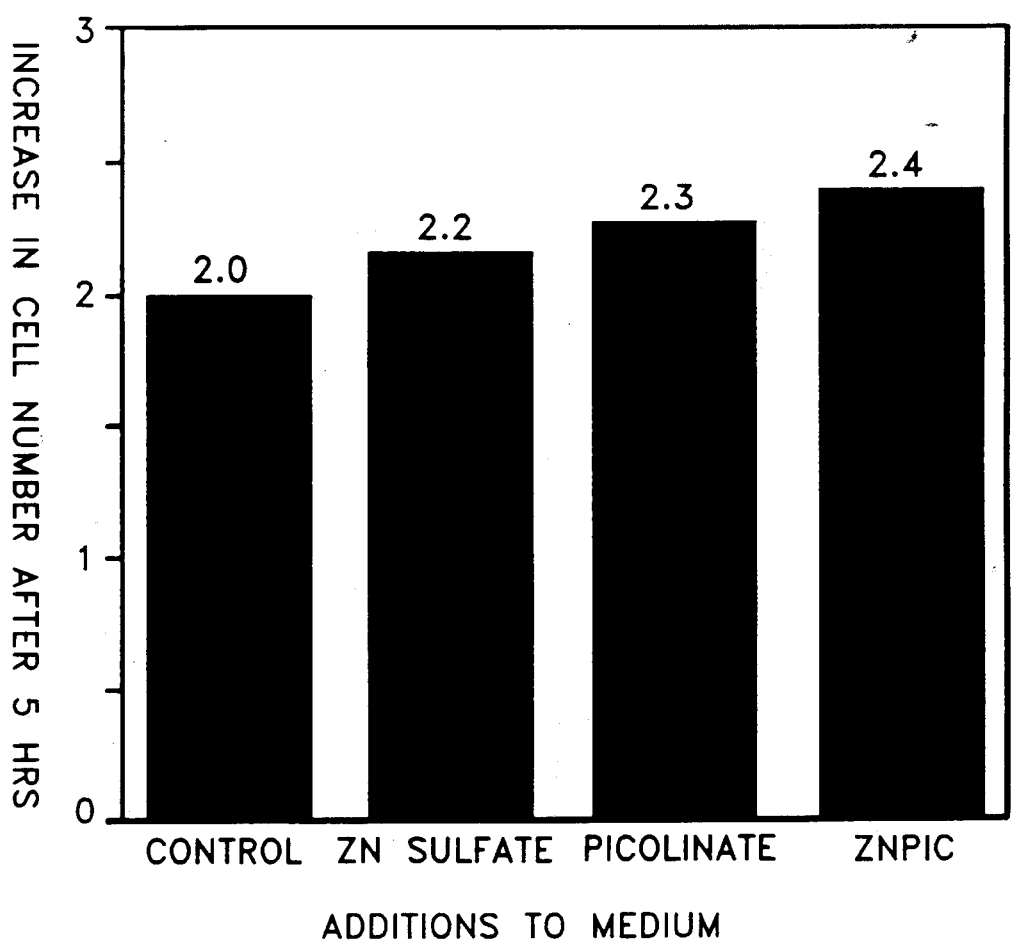
FIG. 1 illustrates the effect of growing yeast cells in deficient media cultures, either in a control, or with added picolinic acid, or a zinc salt (as zinc sulfate or zinc dipicolinate)

The present inventors have now quantitated picolinic acid in yeast and have identified the enzyme picolinic carboxylase in yeast (which is involved in the production of picolinic acid from tryptophan), and designed experiments to compare chromic tripicolinate, zinc dipicolinate, and picolinic acid on their ability to effect oxygen uptake by mouse skin or mouse liver cells.

1. Oxygen Uptake By Skin Cells

In a first series of experiments 0.1 milliliter ("ml") of aqueous solutions of (1) picolinic acid at a concentration of 5 milligrams per milliliter ("mg/ml"), (2) chromic tripicolinate (approximately 1 mg/ml concentration), and (3) zinc dipicolinate (approximately 1 mg/ml concentration), were added to 3.0 ml of a phosphate-glucose buffer media (pH approximately 7.4) that contained 100 mg mouse skin. The rate of oxygen uptake was measured with an oxygen electrode over a period of approximately 1.0 minute until the basal (i.e., control) rate was established, and then the rate with the additive was measured over approximately 10 minutes. It was found that in those samples containing the added picolinic acid, the rate of oxygen uptake increased by 20% over the basal rate, whereas the chromic tripicolinate and zinc dipicolinate did not produce any detectable increase in oxygen uptake. It should be noted that a 20% increase in oxygen uptake with 100 mg of rat skin, would correspond to 2,000 Units of SRF per 0.5 ng of picolinic acid. Thus picolinic acid contains 4,000,000 Units of SRF/g.

2. Oxygen Uptake By Liver Cells

Another series of experiments was performed using the same parameters as described the in the preceding experiment, except that 20 mg of mouse liver cells per 3 ml of media were used rather than the 100 mg of mouse skin cells per 3 ml of media. In this series of experiments, the uptake of oxygen by the cell suspension was increased by 340% in the presence of the picolinic acid (in comparison to the control), whereas the chromic tripicolinate and zinc dipicolinate did not produce any detectable increase in oxygen uptake. In an additional experiment under these same conditions, 15 mg of impure SRF from yeast was added to the same cell suspension, and oxygen uptake increased by 180% over the basal rate. Thus, the 5 mg/ml solution of picolinic acid used in this set of experiments, was 48 times more active than the preparation of crude SRF tested.

The foregoing experiments show then, that picolinic acid (which has now been discovered to be present in yeast), considerably increases oxygen uptake by cells, both in comparison to a control and also in comparison to a preparation of crude SRF extract from yeast. These results indicate that picolinic acid is the SRF factor in previously disclosed yeast extracts. However, to confirm the efficacy of picolinic acid as a factor which may enhance skin healing, a further series of experiments were performed to ascertain the effect of picolinic acid on cell growth. These experiments are detailed below.

3. Growth In Deficient Liquid Media

In a first series of experiments, an isolated pure culture of commercial bakers yeast (sold under the trademark "RED STAR BRAND", available from Universal Foods Corp., Milwaukee, Wisc., U.S.A.) was grown in a complete agar medium sold under the trademark "DIFCO YM" (available from Difco, Inc., Detroit, Mich., U.S.A.), and transferred to a deficient liquid growth medium which is described by Mirsky, et al., *J. Inorg. Biochem.*, Vol. 13, p. 11, (1980). The foregoing deficient medium is free of amino acids and trace metals and contains 2% glucose, vitamins, and minerals needed for cell growth. Various "DIFCO" media are described in detail in "Difco Manual, Culture Media and Reagents for Microbiology", 10th edition, published by Difco Laboratories, Detroit, Mich., U.S.A. (1984). The yeast culture was grown in the deficient medium and then harvested. The resulting cells were then resuspended in a number of aliquots of 25 ml of deficient media to produce in each culture a starting yeast concentration of about 5.5 to $6.0 \times 10^7$ cells/ml. A control culture received no added zinc salt or picolinic acid, while other cultures received sufficient zinc sulfate, picolinic acid, or zinc dipicolinate to produce a resulting concentration of 50 ng of zinc per ml (in the case of zinc sulfate), or 250 ng/ml (in the case of picolinic acid) or 240 ng/ml (in the case of zinc dipicolinate). The cultures were then grown at 30° C. with continuous shaking for five hours. The cell concentration in the cultures was counted again, and the growth increase calculated according to the formula;

Growth Increase = (final cell concentration minus initial concentration) divided by initial cell concentration.

"Growth Increase" is sometimes referred to herein as an increase in cell number or count, and may be expressed as simply a number or as a percent. The increase in cell number (as defined above) was calculated for the samples, and the results (mean, from several experiments) plotted in FIG. 1. As can be seen from FIG. 1, the addition of the picolinic acid produced a 12% greater increase in cell growth under the conditions of the experiments.

4. Growth In Complete Liquid Media

A third series of experiments were performed using the complete medium, "DIFCO YM". The foregoing yeast medium contains a yeast extract, a malt extract, peptone, dextrose, and agar. Sufficient chromic chloride ($CrCl_3$) and chromic tripicolinate were added to respective 100 ml aliquots of the "DIFCO YM" medium to result in a chromium concentration of 0.1 ng/ml in each, while sufficient picolinic acid was added to another aliquot to provide a picolinic acid concentration of 0.8 ng/ml. A 100 ml control aliquot of "DIFCO YM" medium did not receive any chromium or other added growth promoter. Baker's yeast was suspended in each of the 100 ml aliquots to provide an initial cell count as follows:

Initial cell count of control = $3 \times 10^5$ cells/ml; initial cell count in culture to which picolinic acid added=$2.1\times10^5$ cells/ml; initial count in culture to which chromic chloride added=$3\times10^5$ cells/ml; initial cell count in culture to which chromic tripicolinate was added=$2.5\times10^5$ cells/ml.

Figure 2A:
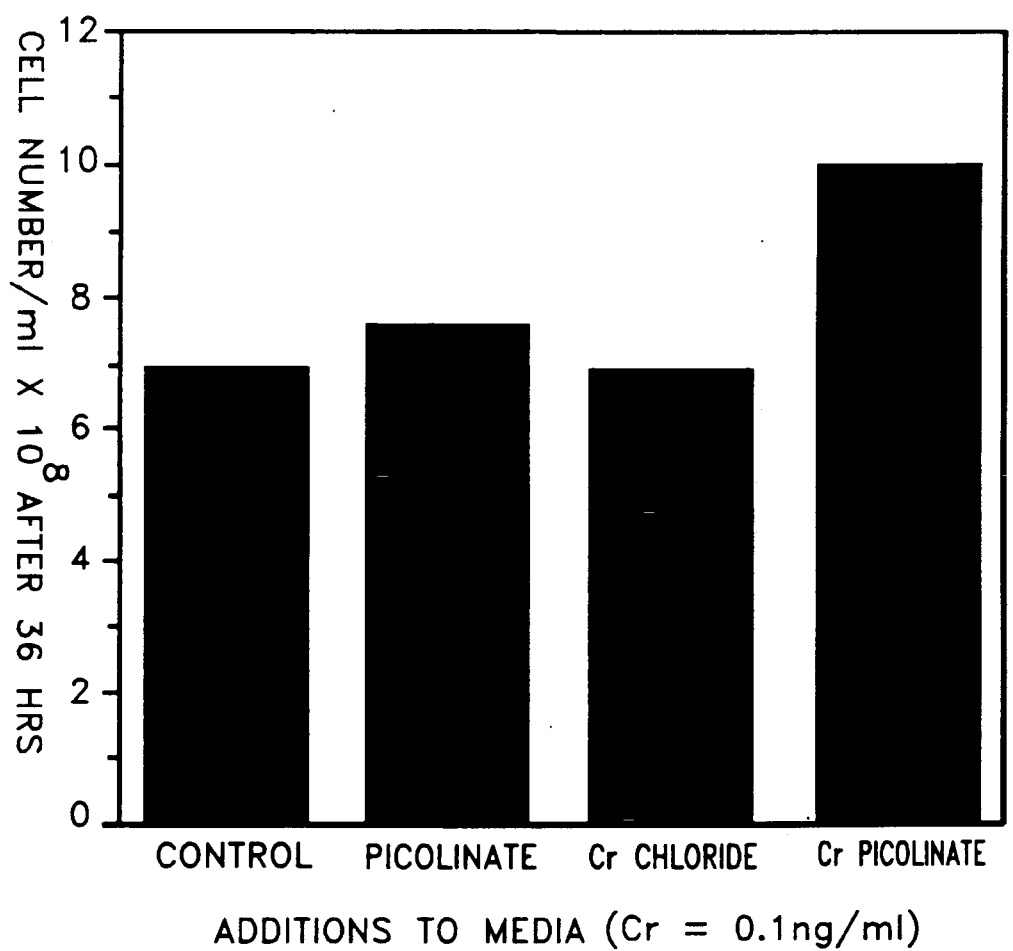
FIG. 2A illustrates the growth of a yeast culture in a complete medium, either in a control, or with added picolinic acid or chromium salt (as chromic chloride or chromic tripicolinate)
Figure 2B:
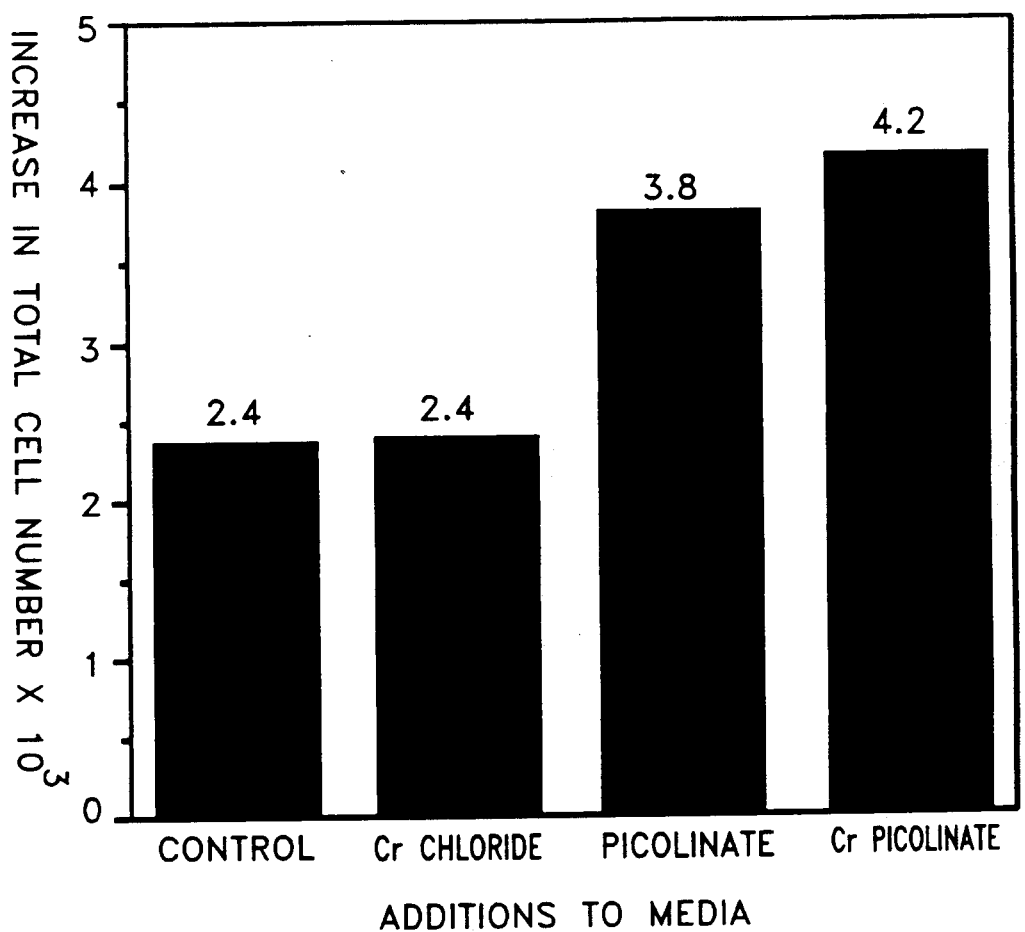
FIG. 2B illustrates the increase in growth found in each of the cultures identified in FIG. 2A, following the incubation period.

The samples were grown at 30° C. for 36 hours. The final cell count of each culture (mean from a number of experiments) is illustrated in FIG. 2A. FIG. 2B illustrates the increase in cell number (mean), as previously defined.

As can be seen from FIG. 2A, the addition of the picolinic acid resulted in an increase of cell concentration which was approximately 56% greater than that of the control or the culture which received added chromic chloride.

5. Growth In Complete Solid Media

In a further series of experiments, supplements were added to potato dextrose agar ("PDA"; in particular a PDA sold under the trademark "BACTO-POTATO DEXTROSE AGAR"; available from Difco, Inc., Detroit, Mich., U.S.A.), a medium approved by a number of organizations for the detection and enumeration of yeasts. Cultures were prepared using a strain of baker's yeast different from that used in the preceding set of experiments. The supplements were added to PDA at the following concentrations (per ml PDA): 400 ng picolinic acid, 40 ng tryptophan. The average yeast colony count was 11% to 18% greater than the count obtained with unsupplemented control cultures as shown in the results below:

| ADDITIONS TO CULTURES | INCREASE IN YEAST CELL COUNT OVER CONTROL COUNT (%) |
| --- | --- |
| Picolinic acid | 11 |
| Picolinic acid + Tryptophan | 18 |

The above results then, illustrate that picolinic acid, now known to be present in yeast (which has been shown to increase the rate of healing of a skin injury), both increases oxygen utilization of cells and additionally increases cell growth. These factors indicate that picolinic acid is also the skin respiratory factor in yeast extracts.

Various modifications and alterations to the embodiments of the invention described above, can of course be conceived by those familiar with the art. Accordingly, the present invention is not limited to those embodiments described in detail, but includes all such modifications and alterations.

We claim:

1. A method of enhancing respiration of mammalian skin, comprising applying to the skin a composition consisting essentially sufficient picolinic acid to provide at least 25,000 units of SRF activity per gram in a carrier selected from the group consisting of an ointment, cream, lotion and spray.

2. The method of claim 1 wherein said picolinic acid is substantially free of impurities from yeast.

3. The method of claim 1 wherein said picolinic acid is prepared from a non-yeast source.

4. The method of claim 1 wherein said picolinic acid is synthetic.

5. The method of claim 1 wherein said composition is applied to injured skin.

6. The method of claim 5 wherein the skin injury is a burn.

7. The method of claim 1 wherein the composition comprises sufficient picolinic acid to provide at least 50,000 Units of SRF activity per gram.

8. The method of claim 1 wherein the composition comprises sufficient picolinic acid to provide at least 500,000 Units of SRF activity per gram.

9. A dressing suitable for application to a mammalian skin injury, comprising:
a bandage; and
picolinic acid in said bandage in a concentration sufficient to provide at least about 25,000 units of SRF activity per gram.

10. The dressing of claim 9 wherein said picolinic acid is substantially free of impurities from yeast.

11. The dressing of claim 9 wherein said picolinic acid is prepared from a non-yeast source.

12. The dressing of claim 11 wherein said picolinic acid is synthetic.

13. A pharmaceutical composition suitable for topical application to the skin consisting essentially of picolinic acid in a concentration sufficient to provide at least about 25,000 units of SRF activity per gram in a carrier selected from the group consisting of an ointment, cream, lotion, and spray.

14. The pharmaceutical composition of claim 13 having sufficient picolinic acid to provide said composition with at least about 50,000 Units of SRF activity per gram.

15. The pharmaceutical composition of claim 14 having sufficient picolinic acid to provide said composition with at least about 500,000 Units of SRF activity per gram.

* * * * *

UNITED STATES PATENT AND TRADEMARK OFFICE
CERTIFICATE OF CORRECTION

PATENT NO. : 5,057,320

DATED : October 15, 1991

INVENTOR(S) : Gary W. Evans, et al

It is certified that error appears in the above-identified patent and that said Letters Patent is hereby corrected as shown below:

Title page, References cited, "Glucose" should be --Gluclose--.

Column 1, line 43, "on" should be --one--.

Column 1, line 55, delete "of".

Column 3, line 45, delete "the". (2nd occurrence)

Signed and Sealed this

Sixteenth Day of March, 1993

Attest:

STEPHEN G. KUNIN

Attesting Officer   Acting Commissioner of Patents and Trademarks